United States Patent
Frank et al.

(10) Patent No.: US 7,699,868 B2
(45) Date of Patent: Apr. 20, 2010

(54) MEDICAL GRIPPING AND/OR CUTTING INSTRUMENT

(75) Inventors: Timothy Graham Frank, Fife (GB); Stuart I. Brown, St. Andrews (GB); Ian Rutherford, Dundee (GB)

(73) Assignee: University of Dundee (GB)

( * ) Notice: Subject to any disclaimer, the term of this patent is extended or adjusted under 35 U.S.C. 154(b) by 159 days.

(21) Appl. No.: 10/891,720

(22) Filed: Jul. 14, 2004

(65) Prior Publication Data
US 2005/0222597 A1 Oct. 6, 2005

(30) Foreign Application Priority Data
Jul. 15, 2003 (EP) .................. 03016022

(51) Int. Cl.
- *A61B 17/00* (2006.01)
- *A61B 17/29* (2006.01)
- *A61B 17/32* (2006.01)

(52) U.S. Cl. .............. 606/205; 606/206; 606/167; 606/1

(58) Field of Classification Search .......... 600/104, 600/136, 141, 146, 147, 22, 533–535, 1, 600/174, 205–207, 167; 242/375.2, 481.8; 604/22, 533–535; 606/1, 174, 205–207, 606/167, 185, 190
See application file for complete search history.

(56) References Cited

U.S. PATENT DOCUMENTS

| | | | | |
|---|---|---|---|---|
| 3,989,049 A | * | 11/1976 | Yoon | .............. 128/831 |
| 5,251,611 A | * | 10/1993 | Zehel et al. | .............. 600/141 |
| 6,053,921 A | | 4/2000 | Wagner et al. | .............. 606/74 |
| 6,099,550 A | | 8/2000 | Yoon | .............. 606/205 |
| 6,214,026 B1 | * | 4/2001 | Lepak et al. | .............. 606/200 |
| 6,755,338 B2 | * | 6/2004 | Hahnen et al. | .......... 227/175.1 |
| 7,169,167 B2 | * | 1/2007 | Chu | .............. 606/205 |
| 2001/0034536 A1 | * | 10/2001 | Looper et al. | .............. 606/205 |

FOREIGN PATENT DOCUMENTS

WO WO 03/101316 A1 12/2003

\* cited by examiner

*Primary Examiner*—Anhtuan T Nguyen
*Assistant Examiner*—Amy T Lang
(74) *Attorney, Agent, or Firm*—St. Onge Steward Johnston & Reens LLC

(57) ABSTRACT

The invention relates to a medical gripping and/or cutting instrument with an instrument shaft (1), with a handle (3) that can be fixed movably on the instrument shaft (1), and with a tool (2) mounted on the distal end of the instrument shaft (1) and consisting of two jaw member (2a, 2b), where at least one jaw member (2a or 2b) of the tool (2) can move in relation to the other jaw member (2b or 2a). In order to provide a medical instrument that, along with good cleaning properties and compact structure, also ensures simple and safe operation, the invention proposes that the handle (3) should include a coupling mechanism both to fix the handle (3) to the instrument shaft (1) and also to operate the at least one movable jaw member (2a or 2b) of the tool (2).

14 Claims, 5 Drawing Sheets

MEDICAL GRIPPING AND/OR CUTTING INSTRUMENT

This application claims priority of pending European Patent Application No. 03 016 022.0 filed Jul. 15, 2003.

FIELD OF THE INVENTION

The invention relates to a medical gripping and/or cutting instrument with an instrument shaft, a movable handle that can be secured on the shaft, and a tool mounted on the distal end of the shaft and consisting of two jaw members, where at least one jaw member of the tool is movable with respect to the other jaw member. In particular with instruments for laparoscopic surgery, medical instruments frequently have shaft lengths of 30 cm and more. This shaft length ensures that even farther removed operating areas can be reached without the need to move the instrumental access. Because, however, instruments are most often used for close-range operating areas, the longest part of the instrument shaft happens to be outside the patient's body. This can cause an unfavorable, uncomfortable posture for the surgeon since the handle for controlling and/or activating the surgical instrument is mounted on the proximal end of the instrument shaft.

This problem is exacerbated with the HALS (Hand Assisted Laparoscopic Surgery) operating technique, in which, in addition to inserting the laparoscope and possibly laparoscopic instruments into the peritoneal cavity, a skin incision is made for inserting one of the surgeon's hands so that the surgeon can perform a better-controlled operation thanks to tactile sense and while observing and controlling by means of a laparoscope. While the surgeon supports the surgery with one hand in the patient's peritoneal cavity, with the other hand he/she activates the laparoscopic instruments. A handle situated far off at the end of the instrument shaft constrains the surgeon's activity to no small degree.

To avoid the aforementioned difficulties, there are known ways to equip medical instrument with a movable handle that can be secured onto the instrument shaft.

A generic medical instrument, for instance, is disclosed in U.S. Pat. No. 6,053,921A. In this medical instrument the handle can be displaced by a spring-loaded clamping mechanism along the longitudinal axis of the instrument shaft. The tool mounted on the distal side of the instrument shaft is activated by means of an activation unit situated on the proximal end of the instrument shaft. This special separation of the handle, on the one hand, and the activation unit, on the other, makes handling this instrument more difficult for the surgeon, especially under spatially hampered working conditions.

It is also common to the state of the art that jaw members of the tool can be activated by one or more Bowden cables proceeding from the handle that can be moved along the instrument axis. The use of the Bowden cable, however, has the disadvantage that Bowden cables are difficult to clean properly.

Consequently, it is the aim of the invention to provide a medical instrument of the aforementioned type, which along with good cleaning properties and compact dimensions ensures simple and safe handling.

This aim is fulfilled by the invention in a manner so characterized that the handle includes a coupling mechanism both to secure the handle onto the instrument shaft as well as to operate the at least one movable jaw member of the tool.

As a result of the inventive design it is possible to ensure the attachment of the handle on the instrument shaft as well as the activation of the tool by means of just one component, namely the coupling mechanism. Through this doubled function of the coupling mechanism, the instrument is highly compact and thus simple and safe for the surgeon to operate. In particular, if an instrument of this kind is employed along with the HALS operating technology, this compact structure with the dual function of the coupling mechanism is advantageous.

According to a first practical embodiment of the invention, the instrument shaft consists of an inner shaft as well as an outer tube coaxially surrounding the inner shaft, and the outer tube is constructed at least partially from several tube segments that can slide independently of one another in the longitudinal direction of the instrument shaft and the handle can be secured on the outside of the outer tube.

With a second embodiment of the invention it is proposed that the instrument shaft consist of an inside push/pull element that forms an inside shaft as well as an outer tube coaxially surrounding the push/pull element, and that the outer tube at least on the proximal side has a longitudinal groove by means of which the coupling mechanism can be engaged with the push/pull element. The push/pull element is activated by the coupling mechanism in this embodiment because the push/pull element, at least in certain segments, is configured in such a way at least axially firm action on the push/pull element by the handle thanks to power connection or form-locking sealing, for instance through the fact that the push/pull element is configured in this area as a rack-and-pinion. It is possible likewise to provide a v-shaped notch in the push/pull element into which a corresponding engaging element of the handle can be pressed.

The handle is advantageously composed of the coupling mechanism, made up of two clamping elements, and of a distancing case positioned between the two clamping elements. While the two clamping elements serve, first, to fix the handle on the instrument shaft and, second, to activate the jaw members of the tool, the distancing case constitutes the actual part by way of which the surgeon grasps the handle to guide the instrument. For this purpose this gripping part is preferably ergonomically designed or else a preferably ergonomically designed grip can be secured on the distancing case.

Stationary fixing of the handle to the outer tube so that the activation of the jaw member is ensured in all axial positions of the handle can advantageously be achieved by having the axial extension of the distancing case is greater than the individual tube segments of the outer tube.

To fix the handle on the instrument shaft and to activate the jaw members of the tool, which are arranged both on the distal end of the inner shaft and also on the distal end of the outer tube, it is proposed with the invention that the clamping elements, advantageously configured as ring disks and pretensioned by a spring element in the direction toward the projection on the distancing case, can be clipped individually and/or jointly opposite the instrument longitudinal axis in such a way that the clamping elements grip the outside of the outer tube or the outside of one of the two tube segments of the outer tubes by clamping them.

The invention calls for the tipping of the clamping element with respect to the instrument's longitudinal axis for clamped gripping of the outer tube by means of at least one spreading device mounted on the distancing case, where there is advantageously one spreading device per clamping element on the distancing case, so that the clamping elements can be tipped in such a way, also independently of one another, that the handle can be fixed in place by tipping just one clamping element on the outer tube.

In a practical embodiment of the invention it is proposed that the spreading devices should be configured as tipping gears equipped with cams.

To activate the tool's jaw members positioned on the distal end of the inner shaft and on the distal end of the outer tube, the tube segments of the outer tube can be slid in the tipped position of the clamping elements by the clamping elements in the longitudinal direction of the instrument shaft, where the axial extension of the tube segment of the outer tube, on whose distal end the one jaw member is positioned, is larger than that of the individual proximal-side tube segments, and preferably equal to a multiple of the axial extension of the individual proximal-side tube segments.

The spreading device to activate the clamping elements can in this case be configured so that in activating the spreading device, first the clamping elements are tipped only for clamped gripping of the outer tube, and only upon further activation of the spreading device are the tube segments slid in relation to the inner shaft. The transition from tipping to sliding here can clearly be arranged to accommodate various pressure forces. Acoustical and visual boundaries are likewise possible. The tube segments are initially held in place by a buffer on the proximal side. On the distal side, the outer tube comprises along a portion of its length many small tube segments and the tube segments may be held in place by means of a spring force pushing the entire outer tube in the proximal direction, toward the buffer. As described in more detail in the Detailed Description of Embodiments below, the application of further pressure on the spreading device after the clamping elements are clamped such as to fix the position of the handle will cause a pressing apart of the clamping elements, which will overcome the spring force and exert a pushing force on the outer tube segments so that they slide longitudinally in the distal direction relative to the inner shaft.

In order, first, to limit the proximal-side sliding function of the outer tube and, second, to be able to displace the inner shaft by way of the slidable outer tube in the direction of the instrument's longitudinal axis, it is proposed with the invention that the outer tube should be shorter than the inner shaft and that the inner shaft on the proximal side should have a buffer, which is preferably configured as a support surface for the proximal end of the outer tube.

It is further proposed with the invention that at least the radially outside peripheral edges of the individual tube segments of the outer tube should be configured as tapered or rounded off in order to be able to push the handle without tilting along the outer tube. The addition round of the radially inner peripheral edges ensures that it can glide on the inner shaft without encumbrance.

To ensure that the jaw members of the tool, after activation, are moved back into the starting position by the coupling mechanism of the handle, the jaw members of the tool are pre-tensioned by means of a spring element into a working position. It is likewise proposed with the invention that at least the part of the outer tube formed by the individual tube segments should be pre-tensioned by means of a spring element in the proximal direction.

It is finally proposed with the invention that the part of the instrument shaft extending beyond the handle on the proximal side in each case should be able to twist at an angle with respect to the distal part of the instrument shaft in order to keep the proximal length of the instrument pointing away from the surgeon as short as possible.

Additional characteristics and advantages of the invention are disclosed with reference to the appended drawings, in which an embodiment of an inventive medical gripping and/or cutting instrument is presented schematically.

DETAILED DESCRIPTION OF EMBODIMENTS

Figure 1:
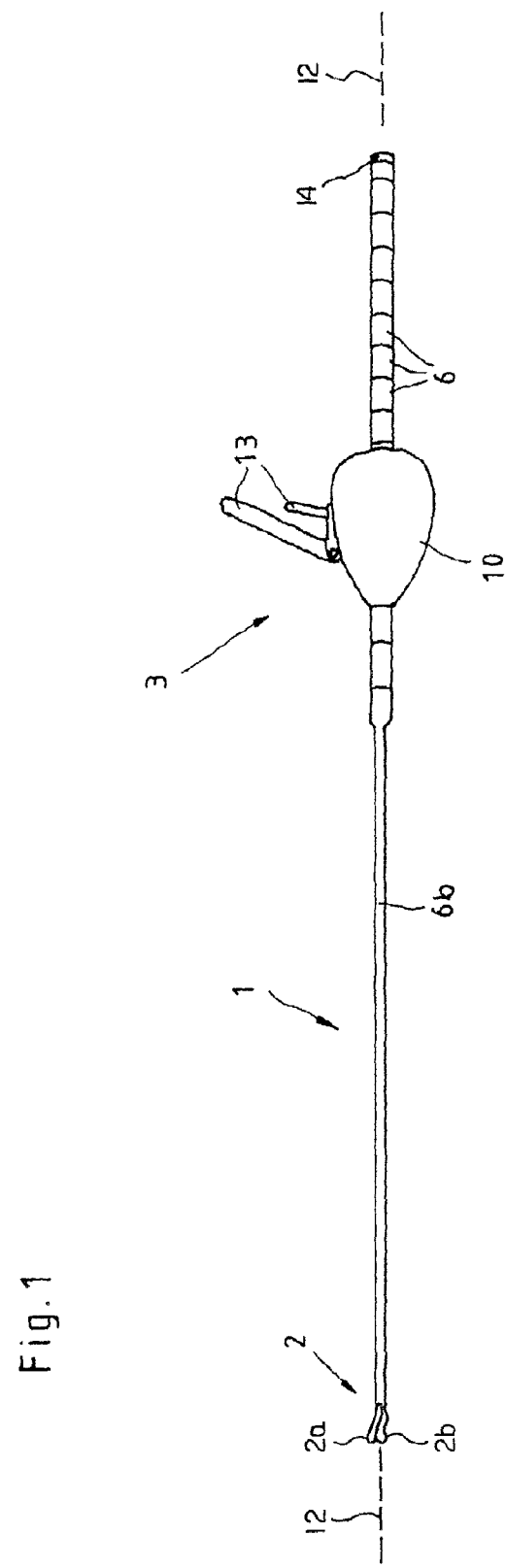
FIG. 1 shows a schematic side view of an inventive medical gripping and/or cutting instrument.

The medical gripping and/or cutting instrument shown in FIG. 1 consists essentially of an extended instrument shaft 1, on whose distal end a tool 2 consisting of two jaw members 2a and 2b is positioned, as well as of a handle 3, which can be fixed onto the instrument shaft to move at least partially along the instrument shaft 1.

Figure 5A:
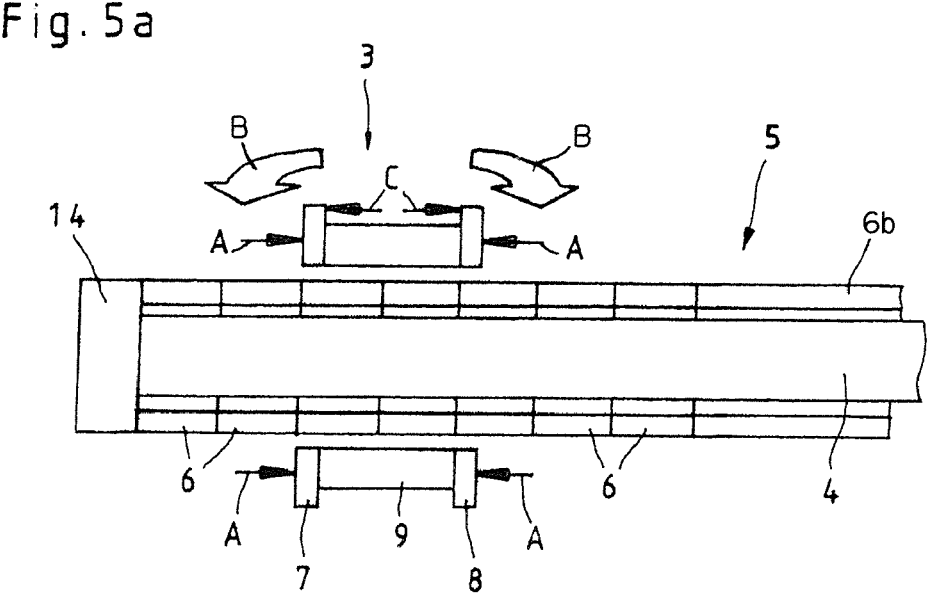
FIG. 5a shows a partial schematic view of the operation of the inventive instrument presenting the instrument in a starting position.
Figure 5B:
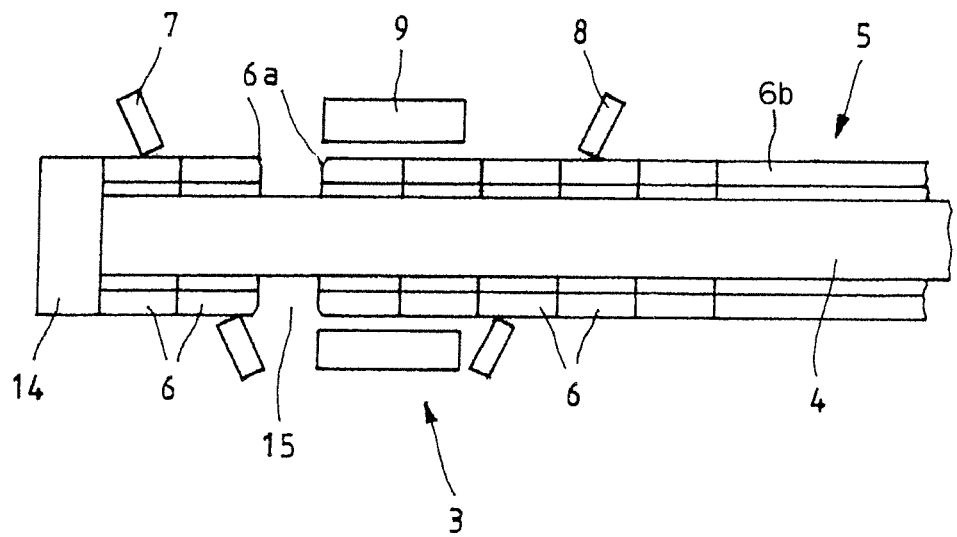
FIG. 5b shows a schematic view as in FIG. 5a but presenting the instrument in a working position.

As can be seen from FIGS. 5a and 5b, the instrument shaft 1 consists of an inner shaft 4 and an outer tube 5 coaxially surrounding the inner shaft 4. The jaw members 2a and 2b of the tool 2, which are positioned on the distal end of the instrument shaft 1, are arranged here so that jaw member 2a is positioned on the distal end of the inner shaft 4 while jaw member 2b is mounted on the distal end of the outer tube 5. The outer tube 5 in the illustrated embodiment consists of several tube segments 6 that can be slid in the longitudinal direction independently of one another, in such a way that the axial extension of the distal tube segment 6b of the outer tube 5, on whose distal end one jaw member 2b is positioned, is equal to a multiple of the axial extension of the individual proximal-side tube segments 6. In addition the distal tube segment 6b has an outer diameter that is reduced with respect to the other tube segments 6.

Although the tube segments 6 in the illustrated embodiment are illustrated as cylindrical tube segments 6 with circular cross-section, this cross-section shape is not compulsory. What's important is that the individual tube segments 6 can be slid in the longitudinal direction of the instrument shaft 1 relative to the inner shaft 4. The tube segments 6 should preferably be positioned on the inner shaft 4 but secure against rotation with respect to the inner shaft 4. This can be achieved, for instance, if the tube segments have grooves or studs and the inner shaft 4 has corresponding studs or grooves, which ensure an exclusively axial mounting of the tube segments 6 relative to the inner shaft 4.

Figure 3:
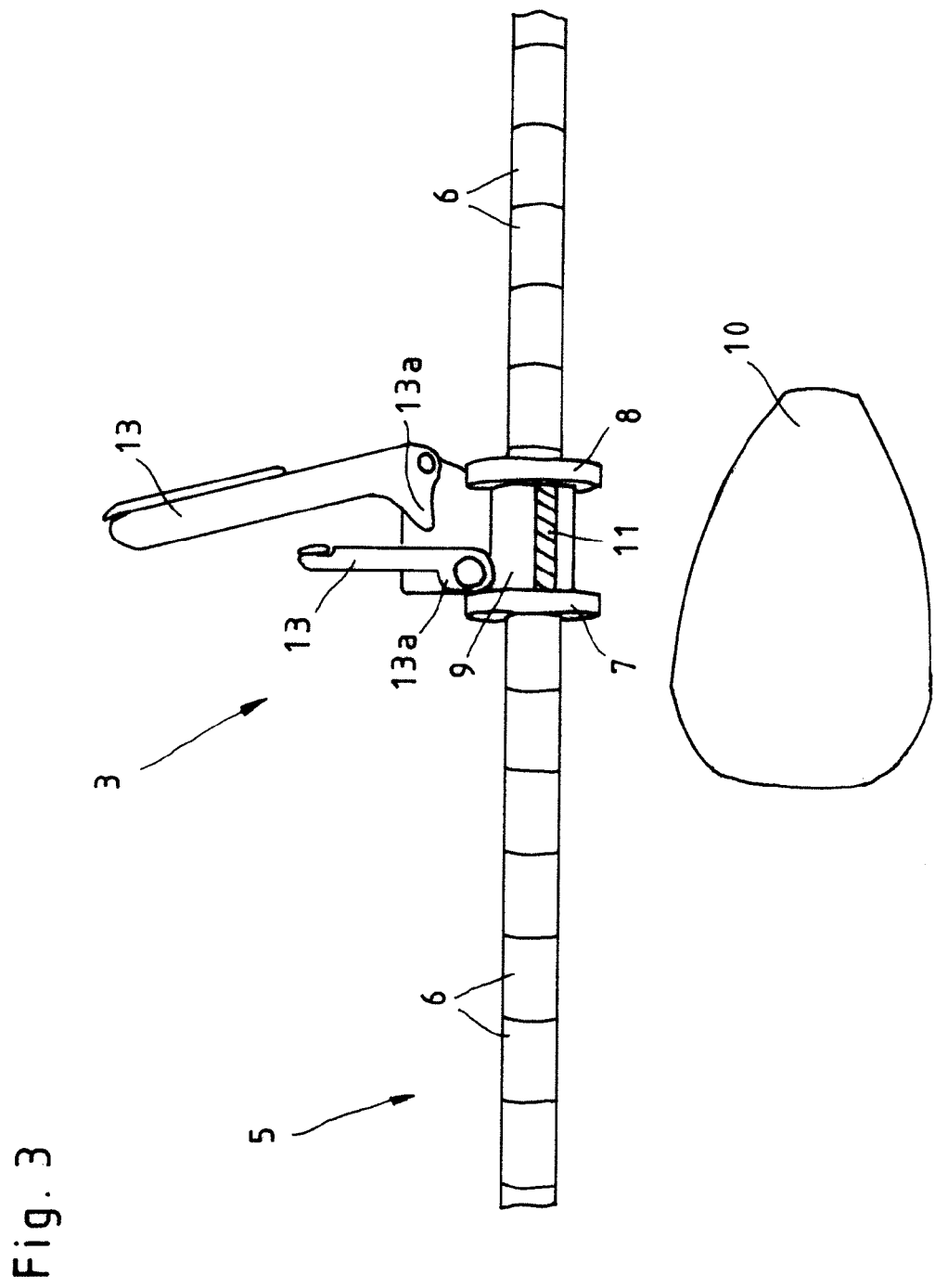
FIG. 3 shows a partial side view, turned at 90 degrees, of the instrument of FIG. 1 but with the gripping part removed.

The handle 3, which can be movably fixed on the instrument shaft 1, consists, as can be seen in particular in FIG. 3, of a coupling mechanism made up of two clamping elements 7, 8 and a distancing case 9 situated between the two clamping elements 7, 8 as well as a gripping part 10 that can be fixed on the distancing case 9, so that the axial extension of the distancing case 9 is greater than that of the individual proximal-side tube segments 6 of the outer tube 5. The coupling mechanism made up of the two clamping elements 7 and 8 serves, first, to fix the handle 3 on the instrument shaft 1 and, second, to activate the tool 2, as described in more detail below.

Figure 4:
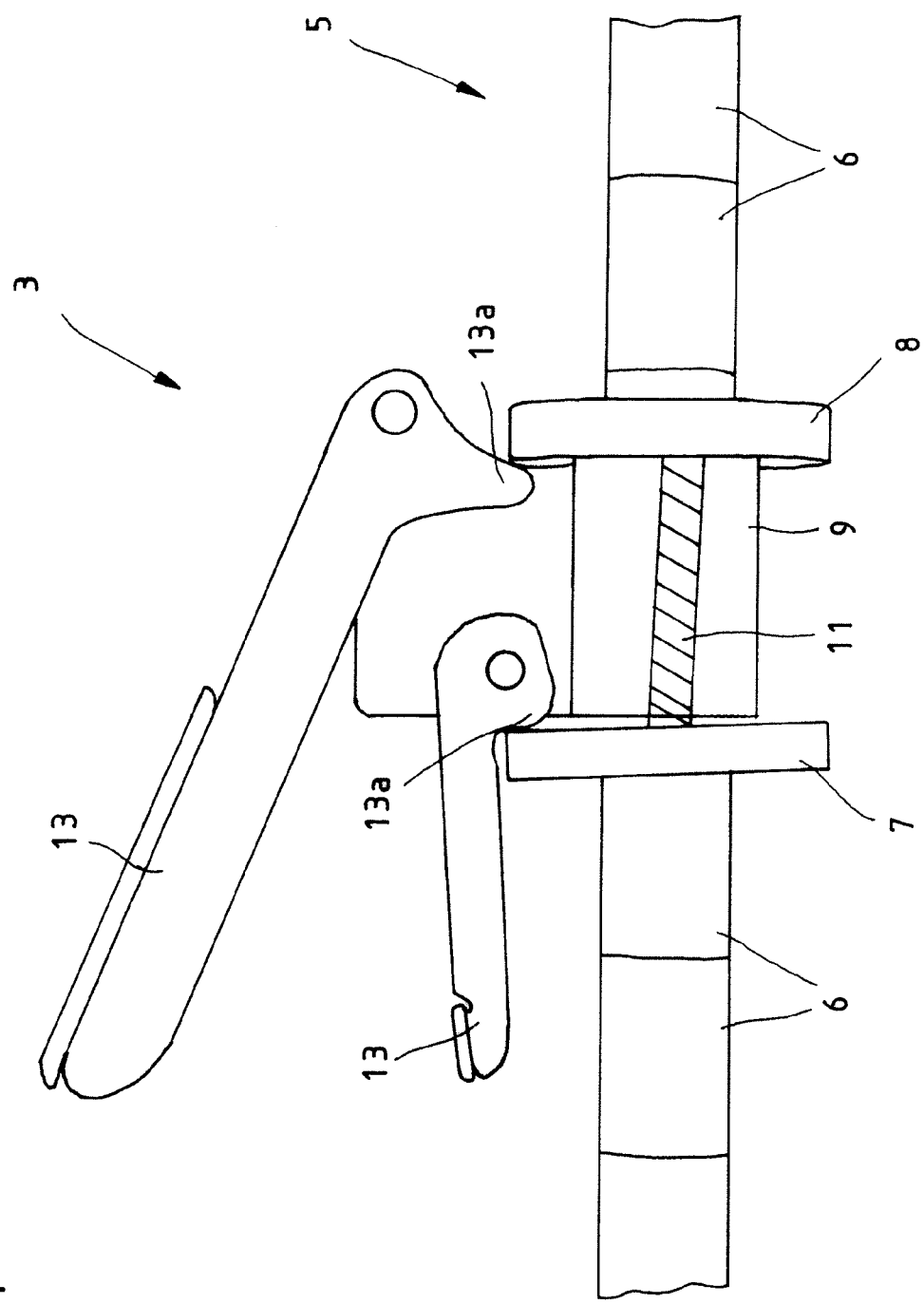
FIG. 4 shows an enlarged partial side view as in FIG. 3 but showing the coupling mechanism in activated state on one side.

As can be seen from FIGS. 4 and 5b, the two clamping elements 7 and 8 of the coupling mechanism of the handle 3, which clamping elements are pre-tensioned by a spring element 11 in the direction toward the projection on the distancing case 9, are tippable toward the instrument longitudinal axis 12 in such a way that the clamping elements 7 and 8 grip the outside of the outer tube 5 in a clamping or tipping motion. To tip the clamping elements 7 and 8, spreading devices are mounted as a rocker arm 13 on the distancing case 9 and impact the clamping elements 7, 8 on one side, by means of configured cams, with such a pressure that the clamping elements 7, 8 configured as ring disks fix themselves on the outside of the outer tube 5 wedging/canted.

In the illustrated embodiment, two rocker arms 13 are mounted on the distancing case so that there is one rocker arm 13 provided for each clamping element 7, 8. This arrangement makes it possible to move the clamping elements 7, 8 independently of one another by way of the respective associated rocker arm 13 into the tipped position with respect to the instrument longitudinal axis 12. Of course it is also possible to tip both clamping elements 7, 8 by means of a common spreading device.

To be able to slide the handle 3 along the outside of the outer tube 5 as free of canting as possible, the outer peripheral edges 6a of the tube segments 6 are tapered or rounded in configuration, as is seen schematically in detailed tube segments in FIG. 5b. In similar manner the inner peripheral edges turned toward the inner shaft 4 can likewise be tapering or rounded in configuration, also in order to ensure that the tube segments 6 can slide along the inner shaft 4 free of canting.

The mode of operation of the illustrated medical gripping and/or cutting instrument is described hereafter, especially with help of the schematic drawings of FIGS. 5a and 5b. FIG. 5a gives a partial, schematic view of the structure of the medical instrument with the inner shaft 4 and the outer tube 5 that surround the inner shaft 4 coaxially and is made up of individual tube segments 6.

The tube segments 6 of the outer tube 5, which are mounted on the inner shaft 4 so that they can freely slide, are pressed together by means of a spring element not shown in the illustration and pre-tensioned in the proximal direction so that the tube segments 6 of the outer tube 5 are directly in contact with a projection 14 situated on the proximal end of the inner shaft 4. As a result of this direct contact of the tube segments 6 on the projection 14 of the inner shaft 4, along with the sliding of individual tube segments 6 toward one another, there is also an immediate relative motion of the inner shaft 4 toward the outer tube 5, and this motion in turn immediately causes an activation of the jaw members 2a and 2b positioned on the distal ends of the inner shaft 4 and of the outer tube 5.

In the starting position illustrated in FIG. 5a, the handle 3 can slide freely along the instrument shaft 1 because pulling forces in the direction of the arrow A are exerted upon the clamping elements 7 and 8 of the coupling mechanism and these forces drive the clamping elements 7, 8 firmly onto the distancing case 9.

If the handle 3 is now to be fixed to the instrument shaft 1, then one or both of the rocker arms 13, which are not shown in these schematic drawings for reasons of simplification, are rotated in the direction of the arrow B, causing the clamping elements 7, 8 to be pressed by the cams 13a of the rocker arm 13 in opposite position to the pulling force of the spring element 11 out of the projection on the distancing case 9 and tipped with respect to the instrument longitudinal axis 12, as can be seen from FIG. 5b and the left-hand part of FIG. 4. By means of the tipping, the corresponding clamping element 7,8 is wedged on the outside of the outer tube 5 and thus fixes the handle 3 on the particular tube segments 6 of the outer tube 5.

To ensure that the tube segments 6 are not deformed or otherwise damaged by the tipping of the clamping elements 7, 8, the individual tube segments 6 of the outer tube 5 are preferably made of a very hard and non-compressible material.

Because the axial extension of the distancing case 9 is greater than that of the individual tube segments 6 of the outer tube 5, the clamping elements 7, 8 of the coupling mechanism wedge themselves in tipping onto various of the tube segments 6 of the outer tube 5 that are mounted so as to be slidable independently of one another on the inner shaft 4.

If the rocker arms 13 are now pressed farther downward in the direction of the arrow B, the clamping elements 7, 8 cannot be tipped further because they are already secured by clamping on the outside of the tube segments 6 of the outer tube. Further activation of the rocker arms 13 thus causes a pressing apart of the clamping elements 7, 8 in the direction of arrow C counter to the spring force of the spring element 11. Because the individual clamping elements 7 and 8 are fixed by wedging on different clamping elements 7, 8 independent of one another, this pressure force in the direction of arrow C causes a pushing of the particular tube segment 6 in the direction of arrow C, so that on the distal side an interval 15 develops between individual tube segments 6.

As can be seen from FIG. 5b, the pushing of the tube segments 6 which are engaged with the clamping elements 7 and 8, as well as of tube elements 6 which are in contact with these tube segments 6, causes on the distal side a pushing of the distal tube segment 6b of the outer tube 5 that is connected with the jaw member 2b, so that the jaw member 2b of the tube 2 is activated, for instance, is moved to a closed position. On the proximal side the pushing of the tube segments 6 directly contacting the buffer 14 of the inner shaft 4 causes the inner shaft 4 to be pushed out of view of the drawing in FIG. 5b toward the left. This displacement of the inner shaft 4 in turn causes an activation of the jaw member 2a positioned on the distal end of the inner shaft 4.

If the rocker arms 13 are moved back into the starting position, in which the cams 13a no longer engage with the clamping elements 7, 8, the clamping elements 7, 8 are pulled back by the spring element 11 into the projection on the distancing case 9, so that the pressure in the direction of arrow C is also removed from the tube segments 6. The jaw members 2a, 2b of the tool 2 are preferably moved back into the, for instance, opened starting position by means of a spring element that is not shown in the illustration. Likewise the tube segments 6 after release of the clamping elements 7, 8 of the coupling mechanism are moved back, by means of the spring element, into the reciprocal projection on one another and on the buffer 14 as shown in FIG. 5a. The pre-tensioning of the jaw members 2a, 2b as well as the pre-tensioning of the tube segments 6 of the outer tube 5 can take place here by means of a common spring element.

Altogether the illustrated medical instrument is distinguished by the double function of the coupling mechanism of the handle 3, made up of the clamping elements 7 and 8, which mechanism makes it possible, first, to fix the handle 3 on any desired position of the instrument shaft 1 and, second, serves to activate the jaw members 2a, 2b of the tool 2.

Figure 2:
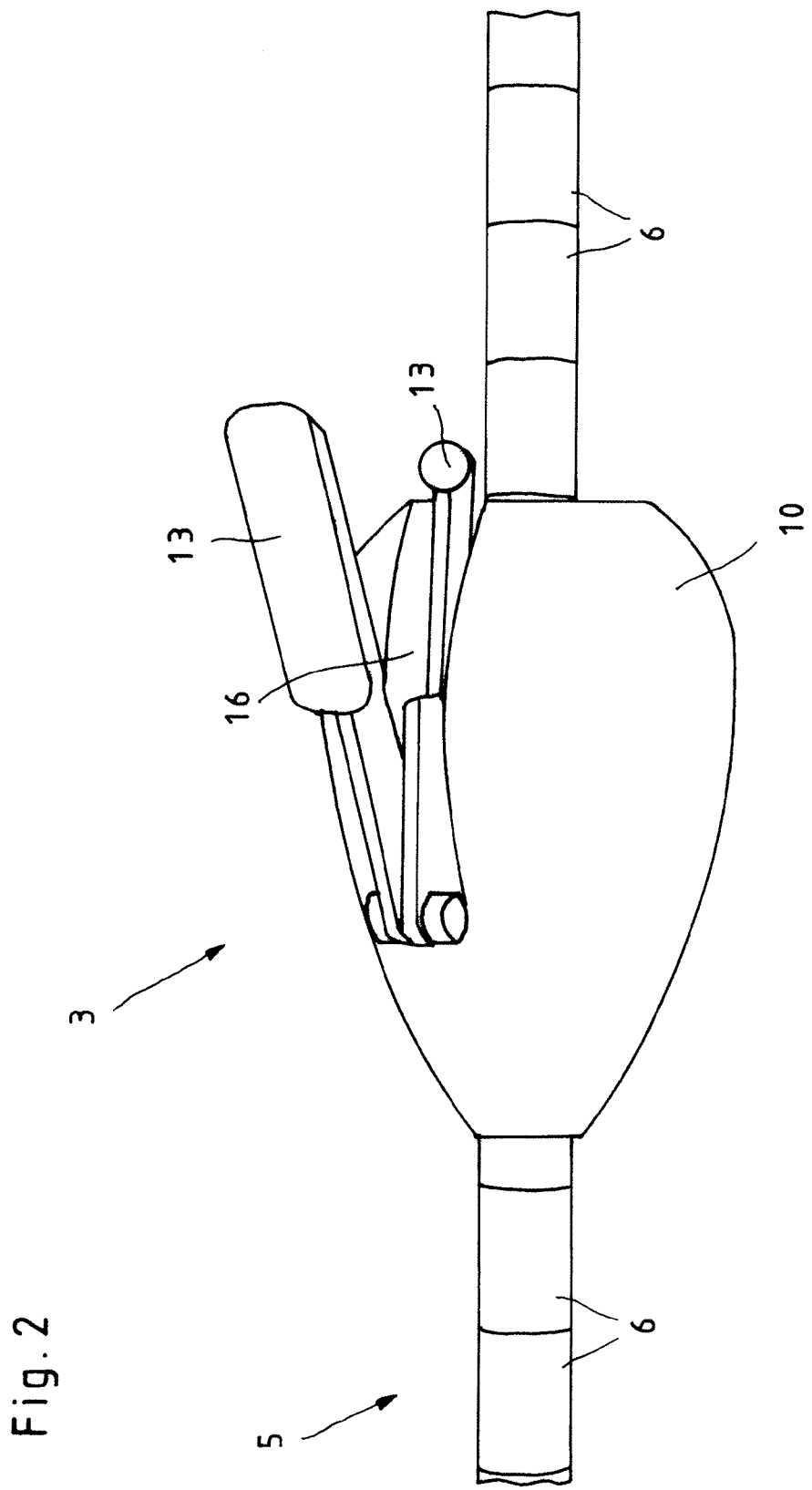
FIG. 2 shows a partial perspective overview of the instrument of FIG. 1.

As can be seen in particular from FIGS. 1 and 2, the handling of the instrument can be simplified if an ergonomically shaped gripping member 10 can be secured on the distancing case 9 of the handle 3. In the present case, this gripping member has an oval "egg shape," and yet any number of other forms are also conceivable, which can be secured in both directions on the instrument shaft. To activate the rocker arms 13, the gripping member 10 of the illustrated embodiment has a groove 16, as can be seen from FIG. 2.

Alternatively to the use of the gripping member 10, it is also possible of course to design the distancing case 9 itself ergonomically so that the surgeon guides the instrument directly over the distancing case 9.

KEY TO ILLUSTRATIONS

1 Instrument shaft
2 Tool
2a Jaw member
2b Jaw member
3 Handle
4 Inner shaft
5 Outer tube
6 Tube segment
6a Peripheral edge
6b Distal tube segment
7 Clamping element
8 Clamping element
9 Distancing case
10 Gripping member
11 Spring element
12 Instrument longitudinal axis
13 Rocker arm
13a Cams
14 Projection
15 Interval
16 Groove
A Arrow
B Arrow
C Arrow

What is claimed is:

1. A medical gripping and/or cutting instrument comprising an instrument shaft, a handle that can be movably fixed in longitudinal direction on the instrument shaft via a coupling mechanism, and a tool positioned on the distal end of the instrument shaft consisting of two jaw members, where at least one jaw member of the tool is movable with respect to the other jaw member, and wherein the coupling mechanism in addition serves to operate the at least one movable jaw member of the tool and that the instrument shaft consists of an inner shaft as well as an outer tube coaxially surrounding the inner shaft, and the outer tube consists at least partly of several tube segments that can slide independently of one another in the longitudinal direction of the instrument shaft and the handle can be secured on the outside of the outer tube;
wherein the handle consists of the coupling mechanism made up of at least two clampinq elements and a distancinq case positioned between the two clamping elements;
wherein the axial extension of the distancing case is greater than that of the individual tube seqments of the outer tube; and
wherein the two clampinq elements are ore-tensioned by means of a spring element in the direction toward the projection on the distancing case.

2. A medical gripping and/or cutting instrument as in claim 1, wherein the clamping elements individually and/or jointly are tippable with respect to the instrument longitudinal axis in such a way that the clamping elements grip the outside of the outer tube by clamping.

3. A medical gripping and/or cutting instrument as claim 2, wherein the clamping elements are configured as ring disks.

4. A medical gripping and/or cutting instrument as in claim 3, wherein the clamping elements can be tipped with respect to the instrument longitudinal axis by means of at least one spreading device positioned on the distancing case.

5. A medical gripping and/or cutting instrument as in claim 4, wherein one spreading device is provided on the distancing case for each clamping element.

6. A medical gripping and/or cutting instrument as in claim 5, wherein the spreading devices are configured as rocker arms equipped with cams.

7. A medical gripping and/or cutting instrument as in claim 6, wherein the tube segments of the outer tube can be slid in the longitudinal direction of the instrument shaft by means of the clamping elements in the tipped position of the clamping elements.

8. A medical gripping and/or cutting instrument as in claim 7, wherein the outer tube is shorter than the inner shaft and the inner shaft on the proximal side has a buffer, which forms a support surface for the proximal end of the outer tube.

9. A medical gripping and/or cutting instrument as in claim 8, wherein one jaw member of the tool is positioned on the distal end of the inner shaft and the other jaw member of the tool is positioned on the distal end of the outer tube.

10. A medical gripping and/or cutting instrument as in claim 9, wherein the axial extension of the tube segment of the outer tube, on whose distal end one jaw member is positioned, equals a multiple of the axial extension of the individual tube segments on the proximal side.

11. A medical gripping and/or cutting instrument comprising an instrument shaft, a handle that can be movably fixed in longitudinal direction on the instrument shaft via a coupling mechanism, and a tool positioned on the distal end of the instrument shaft consisting of two jaw members, where at least one jaw member of the tool is movable with respect to the other jaw member, and wherein the coupling mechanism in addition serves to operate the at least one movable jaw member of the tool and that the instrument shaft consists of an inner shaft as well as an outer tube coaxially surrounding the inner shaft, and the outer tube consists at least partly of several tube segments that can slide independently of one another in the longitudinal direction of the instrument shaft and the handle can be secured on the outside of the outer tube;
wherein at least the radially outside peripheral edges of the individual tube segments of the outer tube are tapering or rounded;
wherein the jaw members of the tool are pre-tensioned into a working position by means of a spring element; and
wherein at least the part of the outer tube made up of the individual tube segments is pretensioned in the proximal direction by means of a spring element.

12. A medical gripping and/or cutting instrument as in claim 11, wherein the distal distancing case is configured ergonomically.

13. A medical gripping and/or cutting instrument as in claim 11, wherein a preferably ergonomically shaped gripping member can be secured on the distancing case.

14. A medical gripping and/or cutting instrument as in claim 13, wherein each part of the instrument shaft extending beyond the handle can be turned at an angle to the distal-side part of the instrument shaft.

* * * * *